US008993294B2

(12) United States Patent
Bodo et al.

(10) Patent No.: US 8,993,294 B2
(45) Date of Patent: Mar. 31, 2015

(54) CROSS-FLOW MEMBRANE FILTRATION-BASED PROCESS FOR PROTEIN RECOVERY

(75) Inventors: Michael Bodo, Cupertino, CA (US); Meng H. Heng, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 336 days.

(21) Appl. No.: 13/389,251

(22) PCT Filed: Aug. 10, 2010

(86) PCT No.: PCT/US2010/044964

§ 371 (c)(1), (2), (4) Date: Apr. 20, 2012

(87) PCT Pub. No.: WO2011/019686
PCT Pub. Date: Feb. 17, 2011

(65) Prior Publication Data
US 2012/0220009 A1 Aug. 30, 2012

Related U.S. Application Data

(60) Provisional application No. 61/232,728, filed on Aug. 10, 2009.

(51) Int. Cl.

| | |
|---|---|
| *C12N 9/00* | (2006.01) |
| *C12P 21/06* | (2006.01) |
| *B01D 61/14* | (2006.01) |
| *B01D 61/16* | (2006.01) |
| *B01D 61/22* | (2006.01) |
| *C07K 14/37* | (2006.01) |

(52) U.S. Cl.
CPC .............. *B01D 61/142* (2013.01); *B01D 61/16* (2013.01); *B01D 61/22* (2013.01); *C07K 14/37* (2013.01); *B01D 2311/04* (2013.01); *B01D 2311/16* (2013.01); *B01D 2311/18* (2013.01); *B01D 2311/2642* (2013.01); *B01D 2315/14* (2013.01); *B01D 2315/16* (2013.01); *B01D 2317/022* (2013.01)

USPC .......................................... 435/183; 435/69.1

(58) Field of Classification Search
CPC .. C07K 14/37; B01D 2315/16; C13B 20/165; C13B 30/02
See application file for complete search history.

(56) References Cited

U.S. PATENT DOCUMENTS

| | | | | |
|---|---|---|---|---|
| 5,262,053 | A | 11/1993 | Meier | |
| 6,903,191 | B2 * | 6/2005 | de Vocht et al. | .............. 530/350 |

(Continued)

FOREIGN PATENT DOCUMENTS

| | | | |
|---|---|---|---|
| EP | 0193046 | A2 | 9/1986 |
| EP | 0363896 | A2 | 4/1990 |

(Continued)

OTHER PUBLICATIONS

Coffman et al., Production and purification of a recombinant Staphylococcal enterotoxin B vaccine candidate expressed in *Escherichia coli.*, Protein Expr. Purif. (2002), vol. 24(2), pp. 302-312.*

(Continued)

*Primary Examiner* — Alexander Kim

(74) *Attorney, Agent, or Firm* — Danisco US Inc.

(57) ABSTRACT

The present methods relate to the isolation and concentration of proteins using cross-flow membrane filtration, and to proteins produced by such methods. A feature of the method is that the protein of interest is retained by a cross-flow membrane under certain conditions that promote retention, while under other condition the protein passes through the membrane.

11 Claims, 6 Drawing Sheets

(56) References Cited

U.S. PATENT DOCUMENTS

| | | | |
|---|---|---|---|
| 7,153,426 B2 * | 12/2006 | van Reis | 210/500.29 |
| 2002/0020668 A1 | 2/2002 | Laustsen et al. | |
| 2008/0237110 A1 * | 10/2008 | Lightfoot et al. | 210/195.2 |

FOREIGN PATENT DOCUMENTS

| | | | |
|---|---|---|---|
| JP | 57206378 A | 12/1982 | |
| WO | 0110470 A1 | 2/2001 | |
| WO | 2008112459 A2 | 9/2008 | |

OTHER PUBLICATIONS

Introduction to TFF PALL Corporation (last viewed on Jan. 16, 2014).*

Marine Microbiology (2001), Edited by John H. Paul, Academic Press, p. 55.*

KOCH Membrane Systems (last viewed on Jun. 9, 2014).*

Aehle Wolfgang, Enzymes in Industry: Production and Applications (2007), 3rd edition, Wiley-VCH, p. 49.

Linder M. et al., FEMS Microbiol Rev. (2005) 29:877-96.

Sunde M. et al., Micron (2008) 39:773-84.

Van Reis R. et al., "High-performance tangential flow filtration using charged membranes," Journal of Membrane Science (1999) 159:133-142.

Wosten H. et al. (2001) Ann. Rev. Microbiol. 55:625-46.

The International Search Report and the Written Opinion for PCT/US2010/44964 dated Dec. 27, 2010.

* cited by examiner

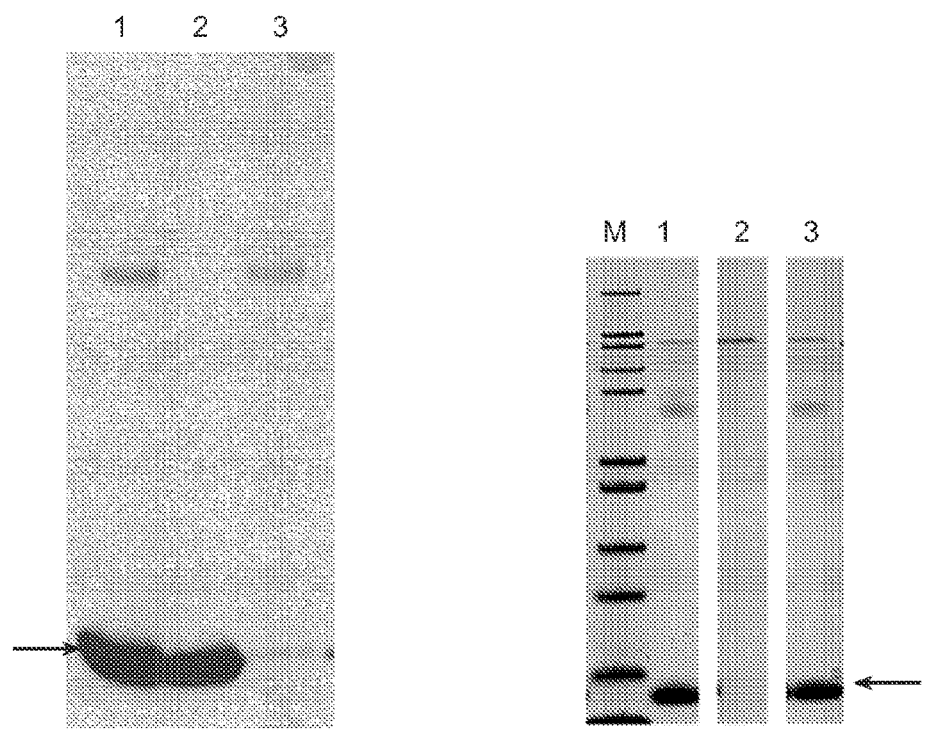
*FIG. 1*  *FIG. 2*
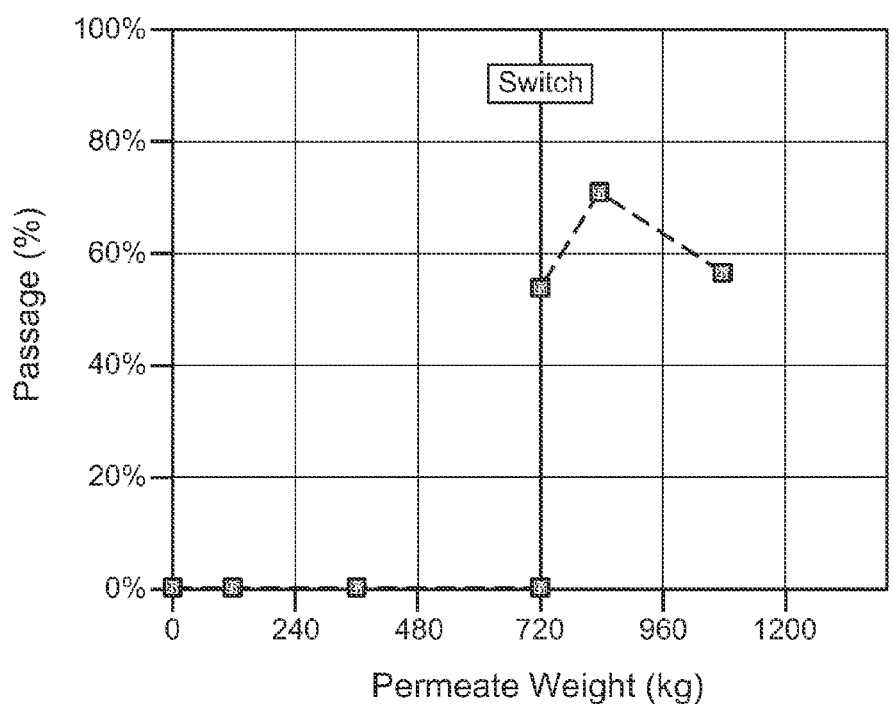
*FIG. 3*

| Cum Perm Weight (g) | Enzyme Passage |
|---|---|
| 100 | 13.1% |
| 503 | 7.4% |
| 995 | 4.0% |
| 1095 | 3.3% |
| 1495 | 2.7% |
| 1986 | 1.8% |
| 2086 | 2.0% |
| 2486 | 1.8% |
| 2961 | 1.1% |

# CROSS-FLOW MEMBRANE FILTRATION-BASED PROCESS FOR PROTEIN RECOVERY

PRIORITY

The present application claims priority under 35 USC §371 to International Application No. PCT/US2010/044964, filed Aug. 10, 2010, which claims the benefit of U.S. Provisional Application Ser. No. 61/232,728, filed on Aug. 10, 2009, each of which are herein incorporated by reference.

TECHNICAL FIELD

The present methods relate to the purification and concentration of proteins using membrane filtration, and to proteins produced by such methods.

BACKGROUND

Conventional recovery and formulation methods relating to proteins produced by microbial fermentation involve several processing steps (e.g., *Enzymes in Industry: Production and Applications* (2007) Wolfgang Aehle, ed., 3$^{rd}$ edition, Wiley-VCH, p. 49; *Bioseparations: Science and Engineering* (2003) R. G. Harrison et al., Oxford University Press, p. 32). Any one of a number of solid-liquid separation methods can be employed to produce a clarified solution containing the protein of interest.

Depending on the desired final product concentration and purity, this clarified liquid containing the protein of interest may meet the requirements for formulation to produce the product. Other times, further processing is required to increase the concentration and/or purity of the protein prior to formulation. Concentration involves dewatering, which, for heat sensitive proteins, is typically achieved by ultrafiltration.

SUMMARY

Described are methods relating to the purification and concentration of proteins using cross-flow membrane filtration, and to proteins produced by such methods.

In on aspect, a method for recovering a protein of interest from a culture solution using cross-flow membrane filtration is provided, comprising: subjecting a culture solution comprising a protein of interest to cross-flow membrane filtration using a first membrane under a first set of conditions that cause the protein of interest to be retained as retentate to allow purification, concentration, and/or buffer exchange of the protein of interest; wherein under a second set of conditions, the first membrane allows the passage of the protein of interest.

In some embodiments, the method further comprising: exposing the protein of interest retained by the first cross-flow membrane to a second cross-flow membrane, under a second set of conditions that cause the protein of interest pass through the second membrane as filtrate to allow purification and/or recovery of the protein of interest.

In some embodiments, the first membrane has a pore size of from about 0.02 µm to about 10 µm. In some embodiments, the first membrane and the second membrane independently have a pore size of from about 0.02 µm to about 10 µm. In some embodiments, the first membrane and the second membrane have substantially the same pore size. In some embodiments, the first membrane and the second membrane are the same membrane. In some embodiments, the first membrane is a series of membranes. In some embodiments, the first and/or second membrane is/are a series of membranes. In some embodiments, a single cross-flow membrane apparatus contains all the membranes used in the method. In some embodiments, the first and second membranes are in separate cross-flow membrane apparatus.

In some embodiments, the culture solution comprising the protein of interest further comprises intact cells or cell debris, and wherein the intact cells or cell debris are retained on the first membrane, along with the protein of interest, under the first set of conditions. In some embodiments, the culture solution comprising the protein of interest further comprises intact cells or cell debris, and wherein the intact cells or cell debris are retained with the protein of interest under the first set of conditions and separated from the protein of interest under the second set of conditions. In some embodiments, the intact cells or cell debris are from filamentous fungi or bacteria. In some embodiments, the culture solution comprising the protein of interest further comprises additional molecules that are not retained by the first membrane.

In some embodiments, the first set of conditions cause the protein of interest to exhibit an apparent molecular weight greater than its true molecular weight. In some embodiments, the second set of conditions cause the protein of interest to exhibit its true molecular weight. In some embodiments, the first set of conditions cause the protein of interest to form multimers, to aggregate, to crystallize, to precipitate, to form a gel, or combinations, thereof.

In some embodiments, the first set of conditions differs from the second set of conditions in transmembrane pressure, cross-flow, and/or solids concentration. In some embodiments, the first set of conditions uses a transmembrane pressure that causes retention of the protein of interest on the first membrane and where the second set of conditions uses a transmembrane pressure that allows permeation of the protein of interest through the second membrane.

In some embodiments, the second set of conditions are in the form of an aqueous solution suitable for formulating the protein of interest into an end product.

In some embodiments, the first set of conditions differs from the second set of conditions in salt concentration, surfactant concentration, polymer concentration, chaotrope concentration, reducing agent concentration, anti-foam concentration, precipitant concentration, pH, or temperature.

In some embodiments, the protein of interest is an enzyme. In some embodiments, the protein of interest is hydrophobin.

In another aspect, a method for recovering a protein of interest from a culture solution using a cross-flow membrane filtration membrane is provided, comprising: (a) applying the culture solution comprising the protein of interest to a cross-flow membrane filtration membrane under a first set of conditions that cause the protein of interest to be retained by the cross-flow membrane filtration membrane; and (b) exposing the protein of interest retained by the cross-flow membrane filtration membrane to a second set of conditions that cause the protein of interest to pass through the cross-flow membrane filtration membrane as filtrate; wherein the protein of interest is first retained by the cross-flow membrane filtration membrane to allow purification and/or concentration and/or buffer exchange, and then passed through the cross-flow membrane filtration membrane to allow cell separation and/or purification and/or recovery.

In some embodiments, the cross-flow filtration membrane of step (a) is different from that employed in step (b). In some embodiments, step (a) and step (b) use the same type of cross-flow filtration membrane.

In some embodiments, both steps are operated in one and the same cross-flow filtration unit apparatus. In some embodiments, each step is operated in a separate cross-flow membrane unit apparatus.

Other embodiments of this aspect of the methods are described above and below.

In another aspect, a protein of interest produced by any of the embodiments of the method is provided. In some embodiments, the protein is an enzyme, a structural protein, or a surface active protein. In particular embodiments, the protein is an amylase or hydrophobin.

These and other aspects and embodiments of the compositions and methods will be apparent from the present description and drawings.

BRIEF DESCRIPTION OF THE DRAWINGS

FIG. 1 is an image of a SDS-PAGE gel showing the protein profiles at different stages of an exemplary microfiltration process. Initial broth (lane 1), permeate product (lane 2), and permeate waste (lane 3). The arrow indicates hydrophobin.

FIG. 2 is an image of a SDS-PAGE gel showing the protein profiles obtained using a conventional microfiltration process. Molecular weight marker (lane M), diluted broth (lane 1), retentate (lane 2), permeate (lane 3). The arrow indicates hydrophobin.

FIG. 3 is a graph tracking the localization of hydrophobin during an exemplary microfiltration process. The word "switch" indicates the point in the process where the diafiltration medium was changed from sodium sulfate to water and the pH of the broth was raised to 5.4.

DETAILED DESCRIPTION

A. Overview of the Method

Figure 4A:
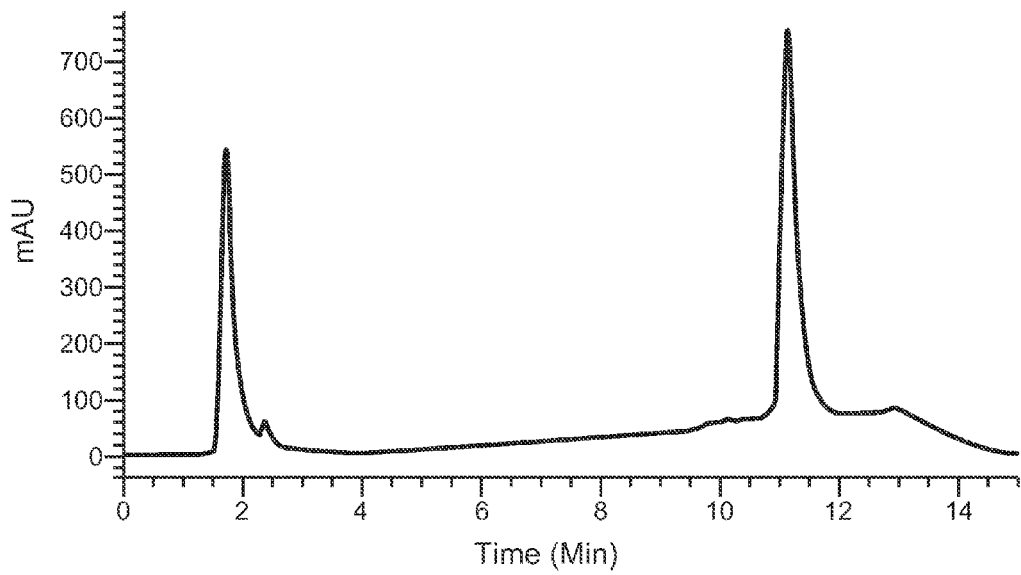
FIG. 4 shows a series of reverse-phase (RP) HPLC traces showing the purification of hydrophobin during an exemplary microfiltration process. Initial broth (A), sodium sulfate permeate (B), and water permeate (C).

Described are methods relating to the recovery of a protein of interest from a culture solution using cross-flow membrane filtration, in which the protein of interest is retained by a cross-flow filtration membrane of a type that would normally allow it to pass. This is accomplished by appropriate conditioning of the culture solution and/or the choice of cross-flow filtration operating conditions. This allows purification of the protein of interest, concentration, and/or buffer exchange.

Also described are methods relating to the purification and concentration of proteins using cross-flow membrane filtration, and to proteins produced by such methods. The methods involve applying a culture solution comprising a protein of interest to a cross-flow membrane filtration membrane under a first set of conditions that cause the protein of interest to be retained by the cross-flow membrane filtration membrane; and then exposing the culture solution retained by the first cross-flow membrane filtration membrane to a second cross-flow membrane filtration under a set of conditions that cause the protein of interest to pass through the second cross-flow membrane filtration membrane into the filtrate. Using this method, the protein of interest is first retained by the cross-flow membrane filtration membrane to allow purification and/or concentration and/or buffer exchange, and then passed through a cross-flow membrane filtration membrane to allow purification and/or recovery. Where the culture solution comprising the protein of interest is a cell broth that includes intact cells and/or cell debris, the present methods allow cell separation and protein concentration to be performed using a single cross-flow filtration membrane. In some cases the resulting protein filtrate can be used directly to formulate an end product.

Microfiltration is conventionally used to retain cell debris and pass proteins, e.g., for cell separation, while ultrafiltration is conventionally used to retain proteins and pass solutes, e.g., for concentration. The present methods uses cross-flow membranes filtration to retain proteins that would otherwise pass into the permeate, an in some embodiments further use cross-flow membranes filtration for cell separation. The present methods are specifically applicable to culture solutions with soluble protein of interest, rather than insoluble protein or inclusion bodies, which would be expected to be retained by a cross-flow filtration membrane. In addition, the present methods can be practiced using aqueous liquids, with no requirement for extraction of retained materials using organic solvents or chaotropic chemicals.

The present methods are particularly useful where the apparent molecular weight of a protein of interest can be manipulated, e.g., by changing the salt concentration, surfactant concentration, polymer concentration, anti-foam concentration, precipitant concentration, pH, temperature, or other parameters in a liquid medium. It is preferable that such manipulations do not irreversibly affect the structure and/or function of the protein of interest.

The present methods are particularly useful when the membrane retention behavior of the protein in solution can controlled by the choice of the operating conditions used in conjunction with the cross-flow membrane filtration membrane. For example, proteins can be caused to be retained on a membrane by using high transmembrane pressure, low cross-flow and high retentate solids content, or combination of these conditions. Conversely, proteins can be caused to pass into the permeate by operating at low transmembrane pressure, high cross-flow, low retentate solids concentration, with vibration, sonication, backpulsing, or air bubbling, or combinations of these conditions.

B. Definitions

Unless defined otherwise, all technical and scientific terms used herein have the same meaning as commonly understood by one of ordinary skill in the art. The following abbreviations and/or terms are defined for clarity.

As used herein, a "protein of interest" is a macromolecule comprising 20 or more contiguous amino acid residues linked by peptide bonds, such as a polypeptide (also referred to as a protein), e.g., an enzyme, a structural protein, a binding protein, and/or a surface-active protein). A protein of interest can be a single protein or a mixture of two or more proteins of interest.

As used herein, a "culture solution" is a liquid comprising the protein of interest and other soluble or insoluble components from which the protein of interest is intended to be recovered. Such components include other proteins, non-proteinaceous impurities such as cells or cell debris, nucleic acids, polysaccharides, lipids, chemicals such as antifoam, flocculants, salts, sugars, vitamins, growth factors, precipitants, and the like. A "culture solution" may also be referred to as "protein solution," "liquid media," "diafiltered broth," "clarified broth," "concentrate," "conditioned medium," "fermentation broth," "lysed broth," "lysate," "cell broth," or simply "broth." The cells, if present, may be bacterial, fungal, plant, animal, human, insect, etc.

As used herein, a protein of interest is in a form in which "the apparent molecular weight is greater than the actual molecular weight" if it is in the form of a multimer (e.g., a dimer, trimer, tetramer, or oligomer), a micelle, a precipitate, an aggregate, a gel, a crystal, a fibril, a plaque, a conjugate, or combinations, thereof.

As used herein, the term "recovery" refers to a process in which a liquid culture comprising a protein of interest and one or more undesirable components is subjected to processes to separate the protein of interest from at least some of the undesirable components, such as cells and cell debris.

As used herein, "cross-flow membrane filtration" refers to a separation technique for liquids that comprises contacting a culture solution containing several soluble or insoluble components with a filtration membrane in an apparatus in a manner that allows the culture solution to flow parallel to the membrane surface and allows at least some of the liquid to penetrate the filtration membrane, thereby separating components in the culture solution into retentate and filtrate. This can also be referred to, in various embodiments, as "membrane separation," "membrane filtration," "tangential flow membrane filtration," "tangential flow filtration," "cross-flow filtration," "microfiltration," or "ultrafiltration."

As used herein, a "filtration membrane," sometimes referred to simply as, a "membrane," is a material that is permeable to liquids and, semipermeable for components dispersed in that liquid, depending on their size, charge, hydrophobicity, or other biophysical properties. The size of particles that can pass through a filtration membrane is determined by its pore size.

As used herein, the terms "filtrate" and "permeate" refer to the material that passes through a membrane. They are used interchangeably.

As used herein, the term "retentate" refers to the material retained by a membrane.

As used herein, "microfiltration" refers to the filtration of liquid through a membrane having a pore size of about 0.02 µm to about 10 µm.

As used herein, "ultrafiltration" refers to the filtration of liquid through a membrane having a pore size of about 0.001 µm to about 0.02 µm.

As used herein, "diafiltration" refers to a membrane based filtration that is used to reduce or remove those components in the retentate that can permeate through the membrane by adding more liquid to the retentate and filtering that additional volume of liquid through the membrane. Diafiltration is sometimes referred to as "buffer exchange".

As used herein, "passage" refers to the movement of a fraction of a component from the retentate through the filtration membrane into the permeate.

As used herein, "retention" refers to the inability of a component to pass from the retentate through the filtration membrane into the permeate.

As used herein, "uniform transmembrane pressure" refers to a cross-flow filtration mode of operation where the pressure difference between the retentate side and the permeate side at the retentate inlet of the cross-flow filter is the same as the pressure difference between the retentate side and the permeate side at the retentate outlet of the cross-flow filter. Uniform transmembrane pressure can achieved, for example, by applying pressure to the permeate at the inlet of the cross-flow filter and restricting the permeate flow at the permeate outlet of the cross-flow filter.

As used herein, the phrase "pressure drop along the membrane element" refers to the pressure difference between the retentate inlet side of a cross-flow membrane filter element and the retentate outlet side of that membrane filter element. In some embodiments, several cross-flow membrane elements are arranged in series in one membrane housing such that the retentate liquid from one element enters the inlet side of the next element in the series. In the case of having multiple elements in one housing, the pressure drop across the entire series of membrane elements equals the "pressure drop along the membrane element" times the number of elements in the housing.

As used herein, a "protein product" refers to a protein preparation suitable for providing to an end user, such as a customer. Protein products may include buffers, salts, preservative, reducing agents, sugars, polyols, surfactants, and the like to prolong the shelf-life of the protein of interest.

As used herein, the singular forms "a," "an," and "the" include plural referents unless the context clearly dictates otherwise. All reference cited herein are incorporated by reference.

C. Cross-Flow Membrane Filtration Recovery Method

The present methods relate to the recovery of proteins using cross-flow membrane filtration, and to proteins produced by such methods. In some cases, the method allows the purification and recovery of such proteins directly from fermentation broth using only a single membrane cross-flow membrane filtration apparatus.

A feature of the present methods is the use of two sets of liquid conditions that differentially affect the retention behavior of the protein of interest. Under the first set of conditions, the protein of interest has an apparent molecular weight that is greater than their actual molecular weight, causing them to be retained by the cross-flow membrane filtration membrane. Examples of protein forms in which the apparent molecular weight that is greater than their actual molecular weight include, but are not limited to, multimers, aggregates, or other supramolecular structures, crystals, precipitates, gels, or combinations, thereof. Under the second set of conditions, the proteins of interest have an apparent molecular weight that allows them to pass through the cross-flow membrane filtration membrane. In this case, the apparent molecular weight may be the actual molecular weight.

Conditions for causing the apparent molecular weight of a particular protein of interest to exceed its actual molecular weight can be determined using conventional methods for sizing macromolecules, including size exclusion chromatography, analytical ultracentrifugation, cross-flow membrane filtration. Exemplary solution conditions that can be manipulated to cause the apparent molecular weight of a protein of interest to exceed its actual molecular weight are the salt concentration, surfactant concentration, polymer concentration, reducing agent concentration, precipitant concentration, pH, or temperature. Such conditions may induce the formation of multimers, aggregates or supramolecular structures, crystals, precipitates, gels, complexes, conjugates, and the like. Generally, the particular form of the protein of interest that allows it to be retained by a cross-flow membrane filtration membrane is not critical, except to the extent that the protein of interest in that form, preferably with the native structure and function, must be retained by the membrane.

Under the first set of solution conditions, membrane filtration is performed to retain, concentrate, or enrich the protein of interest, which cannot pass through the membrane. So long as the conditions maintain the protein of interest in a form where the apparent molecular weight of the protein prevents passage through the membrane, the protein solution can be modified as in the case of desalting, buffer exchange, removing unwanted components, addition of formulation components, and the like.

Retention of the protein of interest can also be increased by the manner in which the cross-flow membrane filtration membrane process is operated. Proteins are retained by cross-flow membrane filtration membranes under conditions of high transmembrane pressure, low cross-flow and/or high retentate solids content. This mode of retention may be combined with the increased retention due to the change in apparent molecular weight of the protein of interest discussed in the previous sections.

Following the retention of the protein of interest, the method then involves altering the conditions of the culture solution to reduce the apparent molecular weight of the protein of interest. In some cases, the conditions cause the protein of interest to behave according to the true molecular weight. The method then involves recovering the protein of interest as filtrate (i.e., permeate or flow-through) from the membrane. In this manner, cells, cell debris, and other insoluble material are retained by the membrane. Other soluble components that have apparent size larger than the cross-flow membrane filtration membrane pore size are retained. The protein of interest previously retained by the membrane now passes through the cross-flow membrane filtration membrane.

The passage of the protein of interest into the permeate in the second step of the method can also be accomplished, for example, by changing the operating conditions of the microfilter to those that facilitate the passage of protein of interest, e.g., low transmembrane pressure, high cross-flow and/or low retentate solids content. Other means of facilitating the passage of the protein of interest known in the art, such as vibration, sonication, backpulsing, or air bubbles, can also be used. Such physical methods for controlling the passage of the protein of interest through the membrane may be combined with each other, as well as with the aforementioned modification of solution conditions to control the apparent molecular weight of the protein of interest.

The method allows a single cross-flow membrane filtration membrane to be used to separate the protein of interest from cells and cell debris, concentrate the protein of interest, and recover the protein of interest in a preselected solution. Proteins of interest recovered by this method may be sufficiently free of other polypeptides and cellular materials and in a sufficient amount and concentration for formulation into a protein product. However, they can be subjected to further purification and/or concentration if desired. The methods have particular application in an industrial setting where overexpressed proteins can be recovered from broth in very few steps, in some cases in sufficient purity and concentration to use directly as a product.

C. Exemplary Proteins for Recovery

The methods can be applied to any enzyme or other protein capable of being induced to have an apparent molecular weight greater than its actual molecular weight by manipulation the solution conditions. Exemplary proteins are enzymes, as exemplified by *Bacillus licheniformis* α-amylase. However, the method can be applied to other enzymes and structural protein.

Another group of exemplary proteins are the hydrophobins, a class of cysteine-rich polypeptides expressed by filamentous fungi. Hydrophobins are small (~100 amino acids) polypeptides known for their ability to form a hydrophobic coating on the surface of objects, including cells and man-made materials. First discovered in Schizophyllum commune in 1991, hydrophobins have now been recognized in a number of filamentous fungi. Based on differences in hydropathy and other biophysical properties, hydrophobins are categorized as being class I or class II.

The expression of hydrophobin conventionally requires the addition of a large amount of one or more antifoaming agents (i.e., antifoam) during fermentation. Otherwise, the foam produced by hydrophobin polypeptides saturates breather filters, contaminates vents, causes pressure build-up, and reduces protein yield. As a result, crude concentrates of hydrophobin conventionally contain residual amounts of antifoam, as well as host cell contaminants, which are undesirable in a hydrophobin preparation, particularly when the hydrophobin is intended as a food additive.

Hydrophobin can reversibly exist in forms having an apparent molecular weight that is greater than its actual molecular weight, which make hydrophobin well suited for recovery using the present methods. Liquid media containing hydrophobin may be combined with the foam or handled separately. Liquid or foam containing hydrophobin can be continuously or periodically harvested from a fermentor for protein recovery as described, or harvested in batch at the end of a fermentation operation. Liquid media containing hydrophobin may be combined with the foam or handled separately.

The hydrophobin can be any class I or class II hydrophobin known in the art, for example, hydrophobin from an *Agaricus* spp. (e.g., *Agaricus bisporus*), an *Agrocybe* spp. (e.g., *Agrocybe aegerita*), an *Ajellomyces* spp., (e.g., *Ajellomyces capsulatus, Ajellomyces dermatitidis*), an *Aspergillus* spp. (e.g., *Aspergillus arvii, Aspergillus brevipes, Aspergillus clavatus, Aspergillus duricaulis, Aspergillus ellipticus, Aspergillus flavus, Aspergillus fumigatus, Aspergillus fumisynnematus, Aspergillus lentulus, Aspergillus niger, Aspergillus unilateralis, Aspergillus viridinutans*), a *Beauveria* spp. (e.g., *Beauveria bassiana*), a *Claviceps* spp. (e.g., *Claviceps fusiformis*), a *Coccidioides* spp., (e.g., *Coccidioides posadasii*), a *Cochliobolus* spp. (e.g., *Cochliobolus heterostrophus*), a

*Crinipellis* spp. (e.g., *Crinipellis perniciosa*), a *Cryphonectria* spp. (e.g., *Cryphonectria parasitica*), a *Davidiella* spp. (e.g., *Davidiella tassiana*), a *Dictyonema* spp. (e.g., *Dictyonema glabratum*), an *Emericella* spp. (e.g., *Emericella nidulans*), a *Flammulina* spp. (e.g., *Flammulina velutipes*), a *Fusarium* spp. (e.g., *Fusarium culmorum*), a *Gibberella* spp. (e.g., *Gibberella moniliformis*), a *Glomerella* spp. (e.g., *Glomerella graminicola*), a *Grifola* spp. (e.g., *Grifola frondosa*), a *Heterobasidion* spp. (e.g., *Heterobasidion annosum*), a *Hypocrea* spp. (e.g., *Hypocrea jecorina*, *Hypocrea lixii*, *Hypocrea virens*), a *Laccaria* spp. (e.g., *Laccaria bicolor*), a *Lentinula* spp. (e.g., *Lentinula edodes*), a *Magnaporthe* spp. (e.g., *Magnaporthe oryzae*), a *Marasmius* spp. (e.g., *Marasmius cladophyllus*), a *Moniliophthora* spp. (e.g., *Moniliophthora perniciosa*), a *Neosartorya* spp. (e.g., *Neosartorya aureola*, *Neosartorya fenneffiae*, *Neosartorya fischeri*, *Neosartorya glabra*, *Neosartorya hiratsukae*, *Neosartorya nishimurae*, *Neosartorya otanii*, *Neosartorya pseudofischeri*, *Neosartorya quadricincta*, *Neosartorya spathulata*, *Neosartorya spinosa*, *Neosartorya stramenia*, *Neosartorya udagawae*), a *Neurospora* spp. (e.g., *Neurospora crassa*, *Neurospora discreta*, *Neurospora intermedia*, *Neurospora sitophila*, *Neurospora tetrasperma*), a *Ophiostoma* spp. (e.g., *Ophiostoma novo-ulmi*, *Ophiostoma quercus*), a *Paracoccidioides* spp. (e.g., *Paracoccidioides brasiliensis*), a *Passalora* spp. (e.g., *Passalora fulva*), *Paxillus filamentosus Paxillus involutus*), a *Penicillium* spp. (e.g., *Penicillium camemberti*, *Penicillium chrysogenum*, *Penicillium marneffei*), a *Phlebiopsis* spp. (e.g., *Phlebiopsis gigantea*), a *Pisolithus* (e.g., *Pisolithus tinctorius*), a *Pleurotus* spp., (e.g., *Pleurotus ostreatus*), a *Podospora* spp. (e.g., *Podospora anserina*), a *Postia* spp. (e.g., *Postia placenta*), a *Pyrenophora* spp. (e.g., *Pyrenophora tritici-repentis*), a *Schizophyllum* spp. (e.g., *Schizophyllum commune*), a *Talaromyces* spp. (e.g., *Talaromyces stipitatus*), a *Trichoderma* spp. (e.g., *Trichoderma asperellum*, *Trichoderma atroviride*, *Trichoderma viride*, *Trichoderma reesii* [formerly *Hypocrea jecorina*]), a *Tricholoma* spp. (e.g., *Tricholoma terreum*), a *Uncinocarpus* spp. (e.g., *Uncinocarpus reesii*), a *Verticillium* spp. (e.g., *Verticillium dahliae*), a *Xanthodactylon* spp. (e.g., *Xanthodactylon flammeum*), a *Xanthoria* spp. (e.g., *Xanthoria calcicola*, *Xanthoria capensis*, *Xanthoria ectaneoides*, *Xanthoria flammea*, *Xanthoria karrooensis*, *Xanthoria ligulata*, *Xanthoria parietina*, *Xanthoria turbinata*), and the like. Hydrophobins are reviewed in, e.g., Sunde, M et al. (2008) Micron 39:773-84; Linder, M. et al. (2005) FEMS Microbiol Rev. 29:877-96; and Wösten, H. et al. (2001) Ann. Rev. Microbiol. 55:625-46.

D. Exemplary Culture Solutions

Culture solutions broadly include solutions comprising the protein of interest and other soluble or insoluble components from which the protein of interest is intended to be separated and recovered. Culture solutions include e.g., fermentation broth, cell suspensions, conditioned media, aqueous lysates, pre-filtered cell-free suspensions, cleared solutions, clarified solutions, concentrated culture solutions, concentrates, and the like.

The culture solution may include intact or lysed cells, including bacterial, fungal, plant, animal, or insect cells. The culture solution may also include other proteins, non-proteinaceous impurities such as cells or cell debris, nucleic acids, polysaccharides, lipids, chemicals such as antifoam, flocculants, salts, sugars, vitamins, growth factors, precipitants, and the like.

E. Exemplary Cross-Flow Membrane Filtration Membranes

The cross-flow filtration membrane suitable for the present method should have pore size or molecular weight cut-off that is greater than the actual size of the protein of interest. Exemplary pore size of the cross-flow filtration membrane is from about 0.02 μm to about 10 μm, e.g., about 0.02 μm, 0.03 μm, 0.04 μm, 0.05 μm, 0.06 μm, 0.07 μm, 0.08 μm, 0.09 μm, 0.1 μm, 0.2 μm, 0.22 μm, 0.3 μm, 0.4 μm, 0.45 μm, 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, and the like. Exemplary molecular weight cutoff is from about 1 kD to about 500 kD, e.g., about 1 kD, 5 kD, 10 kD, 20 kD, 50 kD, 100 kD, 200 kD, 500 kD.

Exemplary membrane materials include polysulfone (PS), polyethersulfone (PES), polyvinylidenefluoride (PVDF), cellulose esters, ceramics, and the like.

Exemplary types of cross-flow filtration membrane elements are spiral wound modules, tubular membranes, hollow fiber membranes, flatsheet membranes, and the like These and other aspects and embodiments of the methods will be apparent from reading the foregoing description and following Examples.

EXAMPLES

The following examples are provided to illustrate the methods but should not be construed as limiting in scope.

Example 1

Protein Recovery From Fermentation Broth

This Example illustrates a process for recovering a protein from fermentation broth using membrane filtration. 160 kg fermentation broth was prepared by culturing *Trichoderma reseei* that expressed recombinant hydrophobin using conventional techniques.

The harvest broth was treated by addition of 40 kg of 10% sodium sulfate and the pH was adjusted to 3.9 with sulfuric acid. The mixture was warmed to 50° C. and held for two hours. This operation produced 200 kg treated harvest broth.

The treated harvest broth was fed to the retentate tank of a cross-flow microfiltration apparatus fitted with a 3.8"×38" spiral wound KOCH MFK-618, 0.2 μm PES membrane. The retentate mass was first reduced to 120 kg by permeating 80 kg of filtrate, and then diafiltered at constant retentate volume with 270 kg of 2.5% (w/w) sodium sulfate solution at 50° C., 0.3 bar uniform trans-membrane pressure, and at 1 bar pressure drop along the membrane element. Based on SDS-PAGE analysis, the vast majority of hydrophobin was retained with the cells.

The membrane permeate was directed back to the retentate tank while the diafiltered broth pH of the recirculating broth was raised to 6.2 by addition of 10% (w/w) sodium hydroxide solution to the retentate tank and the system was operated for 1.4 hours in this mode.

The broth at pH 6.2 was diafiltered with 320 kg of water, and then concentrated to 80 kg. The permeate product was collected and estimated to contain 91% of the hydrophobin supplied in the initial fermentation broth. The average permeate flux for the entire process was about 25 kilograms per $m^2$ per hour. The SDS-PAGE gel in FIG. 1 shows the protein profile of the initial broth (lane 1), the permeate product (lane 2), and the permeate waste (lane 3). Hydrophobin is predominantly found in the in the permeate product.

Example 2

Conventional Microfiltration Recovery of Protein From Fermentation Broth (Comparative Example)

300 kg fermentation broth was prepared using the same method as described in Example 1. The broth was diluted to 1,200 kg with water, and the diluted broth was concentrated to 100 kg by microfiltration under the same conditions as in Example 1. As shown in FIG. 2 the hydrophobin and most of the protein impurities were permeated into the filtrate during the concentration step (lane 3). This is in contrast to the method described in Example 1, where the hydrophobin was selectively retained in the first part of the process and only the impurities permeated into the filtrate.

Example 3

Protein Recovery From Fermentation Broth 120 kg fermentation broth was prepared by culturing *Trichoderma reseei* that expresses recombinant hydrophobin using conventional techniques. The pH was adjusted to 4.0 with sulfuric acid. The mixture was warmed to 50° C. and held for two hours.

Treated broth was diafiltered with 740 kg of 0.5% (w/w) sodium sulfate solution on a microfilter fitted with four 3.8"× 38" spiral wound (KOCH MFK-618, 0.2 μm PES) membranes in series at 50° C., 0.3 bar uniform trans-membrane pressure, and at 0.75 bar pressure drop along each membrane element. Hydrophobin was retained with the cells. The average permeate flux was 30 kilograms per m² per hour.

The permeate was directed back to the retentate tank while the diafiltered broth was recirculated at 0.05 bar uniform trans-membrane pressure. Then the pH was raised to 5.4 by addition of 10% (w/w) sodium hydroxide solution and the system was operated for 1.0 hours in this mode.

The broth at pH 5.4 was then diafiltered with 740 kg of water. The permeate was collected and estimated to contained 98% of the hydrophobin present in the initial fermentation broth. The average permeate flux for the whole process was 30 kilograms per m² per hour. The process yield was 94%.

The graph in FIG. 3 tracks hydrophobin during the microfiltration process. The word "switch" indicates the point in the process where diafiltration medium was changed from sodium sulfate to water and the broth pH was raised to 5.4.

Figure 4B:
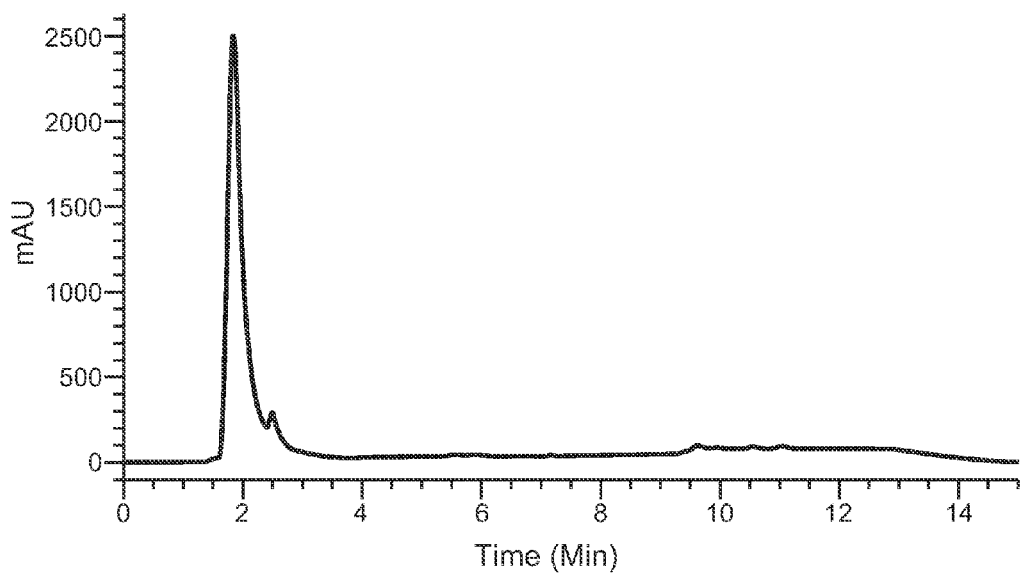
Figure 4C:
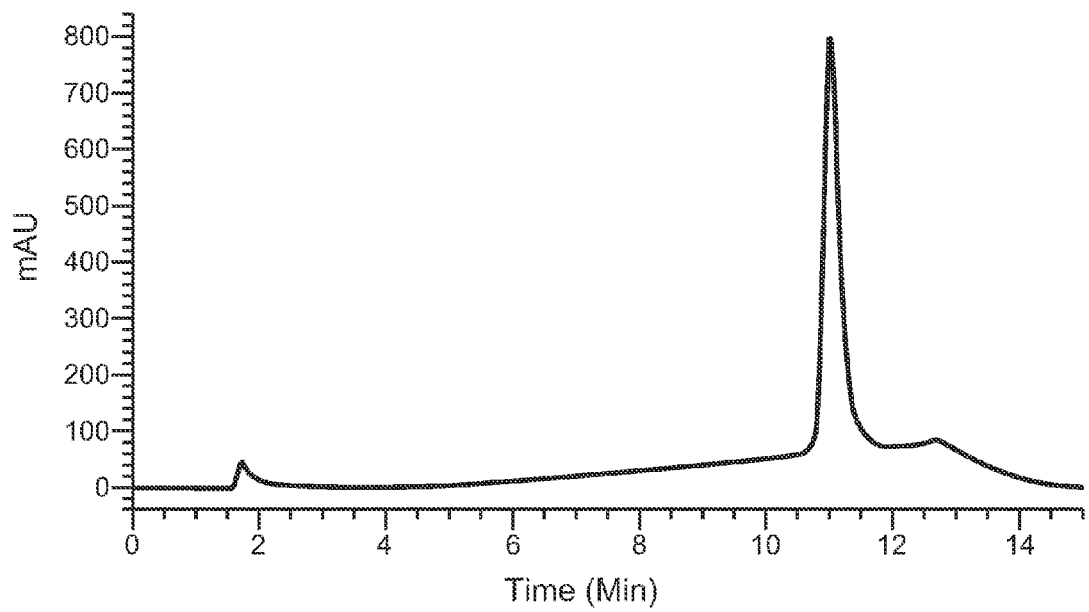

FIG. 4 shown a series of RP-HPLC traces showing hydrophobin in the initial broth (A), sodium sulfate permeate (B), and water permeate (C). Significant purification of hydrophobin was achieved in the process.

Example 4

Enzyme Retention by Manipulating the Fluid Conditions in a Tangential Flow Microfilter

*Bacillus licheniformis* that expressed recombinant α-amylase enzyme, as described in PCT Application No. WO08/112459, was fermented using conventional techniques. Following fermentation, the broth was lysed using 0.01% (w/w) lysozyme for 2 hrs, followed by heat treatment at 60° C. for 2 hr.

The lysed broth was cooled and stored at 10° C. until use. Cold lysed broth was diluted with 1 part of process water, heated to 50° C. in a jacketed tank, and then held for 2 hours with mixing while maintaining pH 6.5±0.2 using 5% NaOH.

Figure 5:
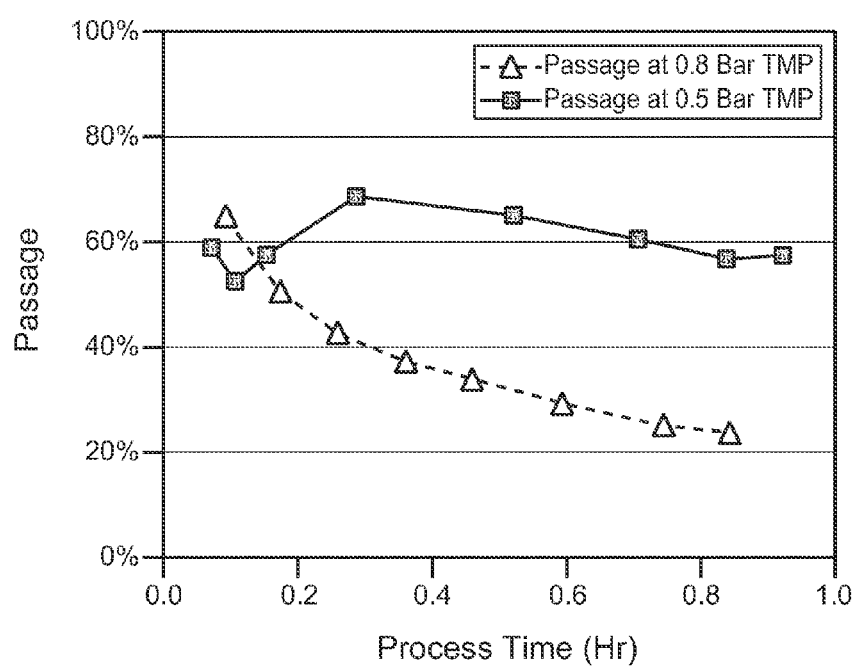
FIG. 5 is a graph tracking the passage of an alpha-amylase from fermentation broth through a microfilter operated at 0.8 bar transmembrane pressure (triangles) and at 0.5 bar transmembrane pressure (squares).

The diluted cell lysate was fed into the retentate tank of a microfiltration skid with a 3.8" spiral wound KOCH MFK-618, 0.2 μm PES microfiltration element, operated at 50° C., 0.8 bar uniform trans-membrane pressure, and 1.3 bar pressure drop along the membrane element. The cell lysate was first concentrated in the microfiltration unit about 3-fold. Then a feed of diluted cell lysate was started to the retentate while at the same time concentrated retentate was removed such that a constant packed solids content of retentate was maintained. As shown in FIG. 5, the enzyme passage continuously declined during the process. A control experiment was run at 0.5 bar uniform transmembrane pressure with the other conditions the same as described above.

Example 5

Protein Recovery From Cell Free Protein Concentrate

This Example illustrates a process for recovering a protein from clarified culture solution using microfiltration.

Clarified culture solution was prepared from fermentation broth described in Example 1 by separating the cells by dead end filtration and dewatering using ultrafiltration. 12 kg of 20% sodium sulfate solution was mixed with 83 kg of this culture solution concentrate, the pH was adjusted to 4.0 with sulfuric acid and the mixture was heated to 50° C. in a jacketed process tank.

Figure 6:
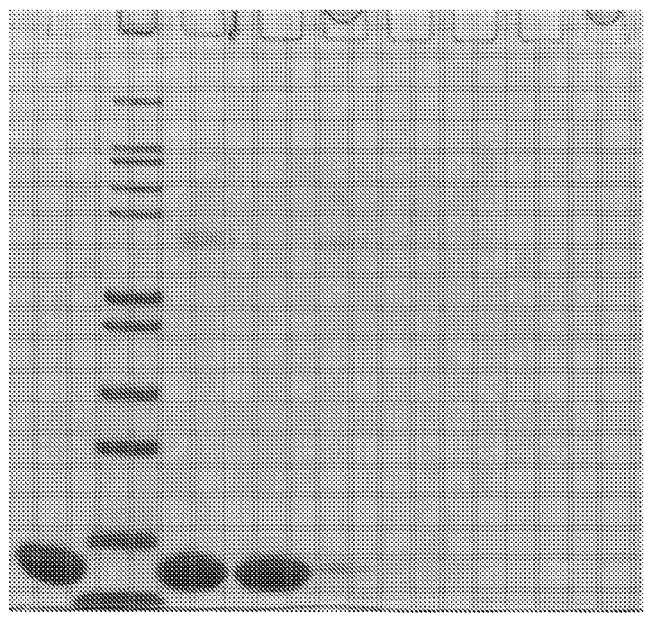
FIG. 6 shows an image of a SDS-PAGE gel showing the protein profiles of various samples obtained during an exemplary microfiltration process. Hydrophobin standard (lane 1), molecular weight marker (lane 2), sodium sulfate treated concentrate (lane 3), sodium sulfate diafiltered concentrate (lane 4), cumulative sodium sulfate permeate (lane 5), sodium sulfate permeate at the start of the process (lane 6), sodium sulfate permeate at 83 kg cumulative permeate (lane 7), sodium sulfate permeate at 166 kg cumulative permeate (lane 8), sodium sulfate permeate at 250 kg cumulative permeate (lane 9).

The mixture was diafiltered with 240 kg of 2.5% sodium sulfate solution by microfiltration in the same system and under the same operating conditions as were used in Example 1. The average flux was 25 KMH. As is shown in FIG. 6, the hydrophobin protein was largely retained by the microfiltration membrane, whereas all the protein impurities were removed into the permeate.

Example 6

Enzyme Recovery and Formulation From Fermentation Broth

This Example illustrates a process that produces formulated, purified enzyme from a fermentation broth on a single microfiltration unit operation.

2.2 kg of fermentation lysate was adjusted to pH 5 using 20% acetic acid. The adjusted lysate was incubated at 50° C. with 80 rpm shaking for 44 hours. 2 kg of the prepared broth were placed into a Sepa Cell benchtop tangential flow filtration module fitted with a flat sheet Microdyn 0.05 μ PES microfiltration membrane, catalog number PM MP005. The system was operated at 5 liters/min cross-flow, 0.7 bar inlet pressure and 50° C. with retentate recirculation. The fermentation lysate was diafiltered with 3.7 kg of 50 mM sodium acetate buffer. 95% of the amylase was retained in the retentate after this step.

The diafiltered lysate was mixed with 8.7 parts (w/w) of DI water and 5.3 parts (w/w) of 70% (w/w) sorbitol and 0.0012 parts (w/w) calcium chloride adjusted to pH 6.5 with sodium hydroxide solution. The mixture was incubated for 12 hours at 50° C.

The lysate/sorbitol/calcium chloride mixture was then concentrated on the same Sepa Cell unit under the same operating conditions, except for the inlet pressure, which was maintained at 0.4 bar. The clear sorbitol/calcium chloride permeate was collected and contained 70% of the amylase enzyme.

Figure 9:
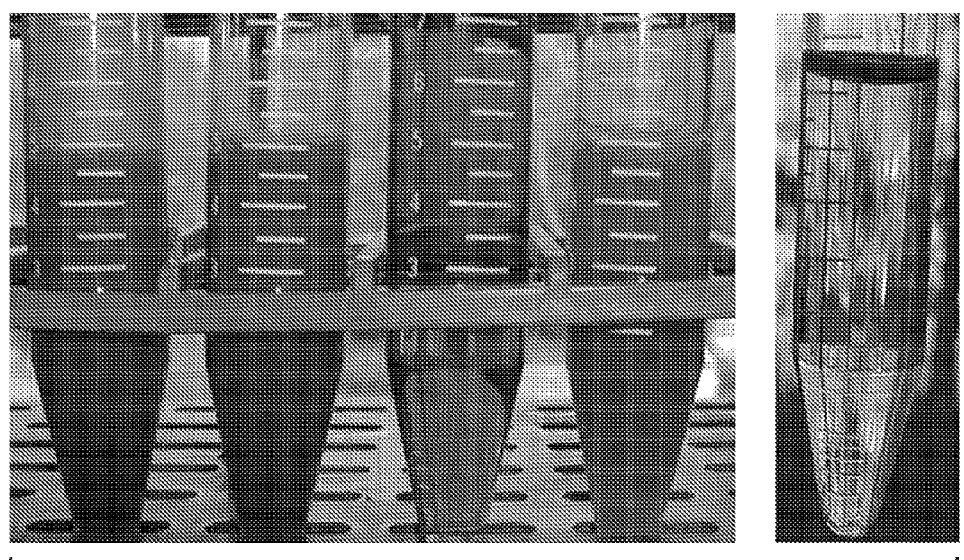
FIG. 9 is an image showing the physical appearance of the products lysate (tube 1), treated lysate (lane 2), sodium acetate buffer permeate (lane 3), diafiltered lysate in sorbitol/water/calcium chloride (lane 4), and sorbitol/calcium chloride permeate (lane 5), from an exemplary microfiltration process.
Figure 7:
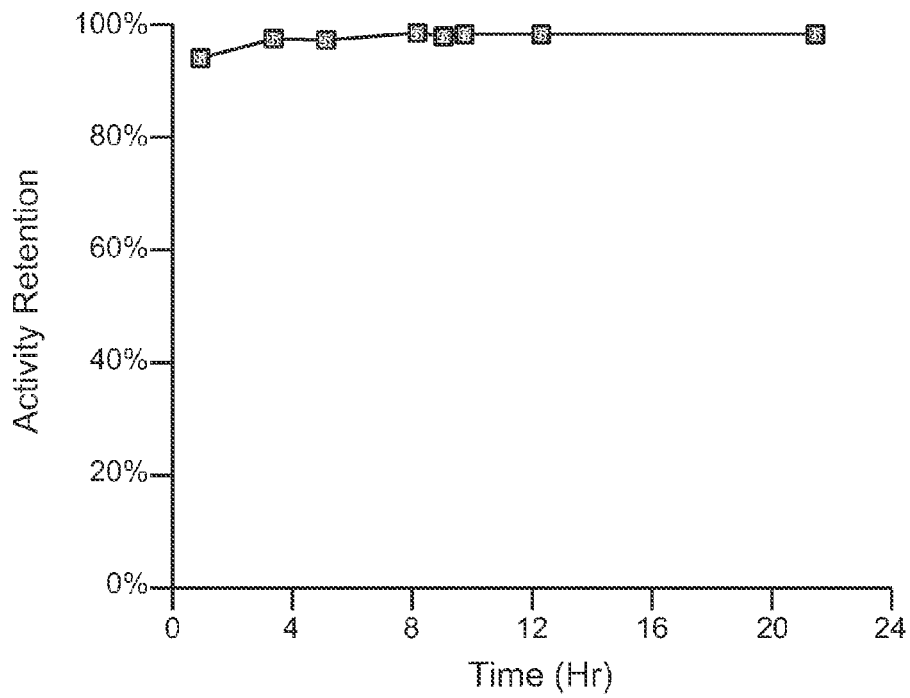
FIG. 7 is a graph showing the retention of hydrophobin over the course of an exemplary microfiltration process. The hydrophobin concentration in the retentate remains constant during diafiltration with sodium acetate buffer.
Figure 8:
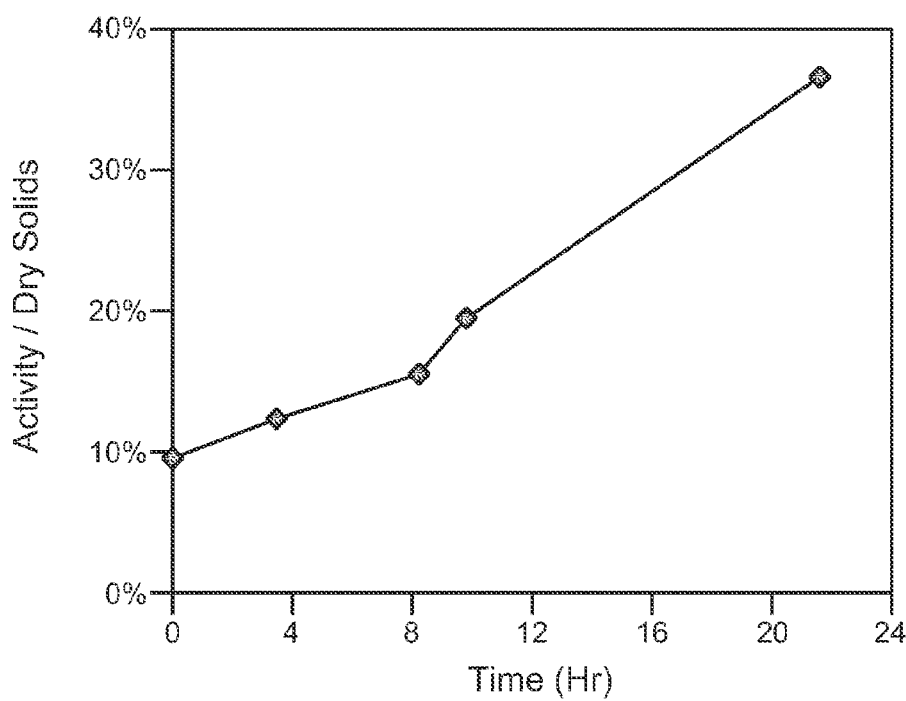
FIG. 8 is a graph showing the activity-to-dry solids ratio of hydrophobin over the course of an exemplary microfiltration process. The enzyme purity increases over time as inactive dry solids are removed with the diafiltration buffer.

The graph in FIG. 7 shows that the activity of enzyme is retained throughout the microfiltration process. The graph in FIG. 8 shows the activity-to-dry solids ratio during the first microfiltration process. Enzyme purity increases as inactive dry solids are removed with the diafiltration buffer. The image in FIG. 9 shows the physical appearance of the lysate (tube 1), treated lysate (tube 2), sodium acetate buffer permeate (tube 3), diafiltered lysate in sorbitol/water/calcium chloride (tube 4), and sorbitol/calcium chloride permeate (tube 5).

Example 7

Enzyme Recovery and Formulation From Cell Free Enzyme Concentrate

This Example illustrates a process similar to that described in Example 6, but for recovering an enzyme from a clarified culture solution. 2 kg of cell free enzyme concentrate was adjusted to pH 5 with acetic acid and incubated with mixing at 50° C. for 44 hours. The prepared concentrate was diafiltered with 50 mM sodium acetate pH 5 on the same apparatus and under the same operating conditions as for the cell-containing lysate in Example 6.

The diafiltered enzyme concentrate was blended in the microfiltration retentate reservoir with 0.25 parts water, 0.0012 parts calcium chloride and 0.35 parts 70% sorbitol and the pH was raised to 6.5 with sodium hydroxide solution.

The enzyme/sorbitol/calcium chloride mixture was microfiltered under the same conditions as the enzyme concentrate, except that the inlet pressure was lowered to 0.5 bar.

Figures 10, 11:
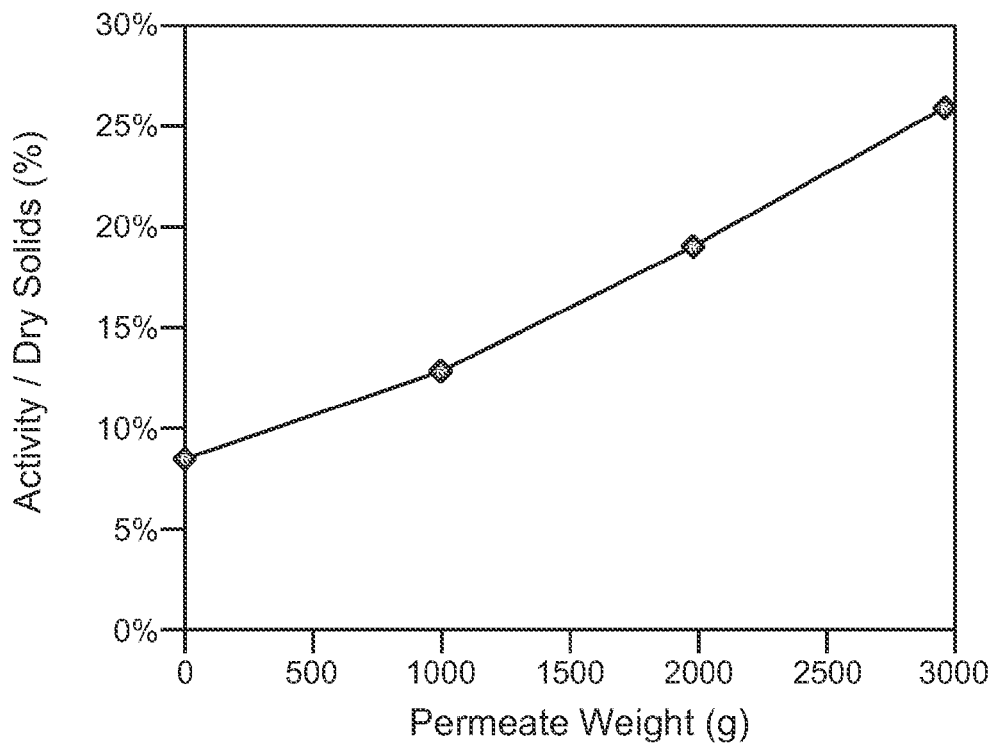
FIG. 10 is a graph showing the activity-to-dry solids ratio of hydrophobin over the course of an exemplary microfiltration process. The enzyme purity increases over time as inactive dry solids are removed with the diafiltration buffer.
FIG. 11 is a table showing enzyme passage during the course of the microfiltration process. Passage refers to the ratio of permeate activity and retentate activity. As the permeate volume increased, enzyme passage slowed.

The graph in FIG. 10 shows the activity-to-dry solids ratio during the first microfiltration process. The enzyme purity increased as inactive dry solids were removed with the diafiltration buffer. The Table in FIG. 11 shows enzyme passage during the course of the microfiltration process. Passage refers to the ratio of permeate activity and retentate activity. As the permeate volume increased, enzyme passage slowed.

What is claimed is:

1. A method for recovering a protein of interest from a culture solution using cross-flow membrane filtration, comprising:
    subjecting a culture solution comprising a protein of interest to cross-flow membrane filtration using a first cross-flow membrane under a first set of conditions that cause the protein of interest to be retained as retentate to allow purification, concentration, and/or buffer exchange of the protein of interest;
    exposing the protein of interest retained by the first cross-flow membrane to a second cross-flow membrane under a second set of conditions under which the apparent molecular weight of the protein of interest is reduced such that it passes through the second membrane as filtrate to allow purification and/or recovery of the protein of interest;
    wherein the first and the second cross-flow membrane are the same type of cross-flow filtration membrane and have a pore size that provides a molecular weight cut-off that is greater than the actual molecular weight of the protein of interest;
    characterized in that the first set of conditions causes the protein of interest to form multimers, to aggregate, to crystallize, to precipitate, to form a gel, or combinations thereof.

2. The method of claim 1, wherein the first membrane has a pore size of from about 0.02 µm to about 10 µm.

3. The method of claim 1, wherein the first membrane and the second membrane are the same membrane.

4. The method of claim 1, wherein the first and/or second membrane is a series of membranes.

5. The method of claim 1, wherein the culture solution comprising the protein of interest further comprises intact cells or cell debris, and wherein the intact cells or cell debris are retained on the first membrane, along with the protein of interest, under the first set of conditions.

6. The method of claim 1, wherein the culture solution comprising the protein of interest further comprises intact cells or cell debris, and wherein the intact cells or cell debris are retained with the protein of interest under the first set of conditions and separated from the protein of interest under the second set of conditions.

7. The method of claim 1, wherein the intact cells or cell debris are from filamentous fungi or bacteria.

8. The method of claim 1, wherein the culture solution comprising the protein of interest further comprises additional molecules that are not retained by the first membrane.

9. The method of claim 1, wherein the second set of conditions are in the form of an aqueous solution suitable for formulating the protein of interest into an end product.

10. The method of claim 1, wherein the first set of conditions differs from the second set of conditions in salt concentration, surfactant concentration, polymer concentration, chaotrope concentration, reducing agent concentration, antifoam concentration, precipitant concentration, pH, or temperature.

11. The method of claim 1, wherein the protein of interest is hydrophobin.

* * * * *